United States Patent [19]
Schick

[11] Patent Number: 5,534,152
[45] Date of Patent: Jul. 9, 1996

[54] INLET FILTER AND METHOD OF USING SAME

[75] Inventor: Hans G. Schick, Anacortes, Wash.

[73] Assignee: Upchurch Scientific, Inc., Oak Harbor, Wash.

[21] Appl. No.: 298,757

[22] Filed: Aug. 31, 1994

Related U.S. Application Data

[62] Division of Ser. No. 41,481, Apr. 1, 1993, Pat. No. 5,366,620.

[51] Int. Cl.$^6$ .................................................. B01D 15/08
[52] U.S. Cl. ........................... 210/656; 210/767; 210/791
[58] Field of Search ................................. 210/656, 767, 210/791, 232, 238, 198.2, 450, 452, 458, 461, 463; 95/82; 96/101, 106

[56] References Cited

U.S. PATENT DOCUMENTS

| | | | |
|---|---|---|---|
| 60,311 | 12/1866 | Wiley | 210/458 |
| 781,536 | 1/1905 | Loffler | 210/461 |
| 1,370,470 | 3/1921 | Martel | 210/461 |
| 2,932,398 | 4/1960 | Korte | 210/452 |
| 3,633,752 | 1/1972 | Kurpgeweit | 210/450 |
| 3,744,640 | 7/1973 | Grover | 210/463 |
| 3,760,949 | 9/1973 | Carey | 210/450 |
| 4,107,043 | 8/1978 | McKinney | 210/463 |
| 4,265,752 | 5/1981 | O'Banion | 210/452 |
| 4,448,684 | 5/1984 | Paradis | 210/198.2 |
| 4,805,525 | 2/1989 | Bivens | 210/461 |
| 4,888,112 | 12/1989 | Kronwald | 210/198.2 |
| 4,994,180 | 2/1991 | Sims | 210/198.2 |
| 5,130,022 | 7/1992 | Chara | 210/450 |
| 5,188,730 | 2/1993 | Kronwald | 210/198.2 |
| 5,240,607 | 8/1993 | Asay | 210/450 |
| 5,275,723 | 1/1994 | Greenley | 210/198.2 |

*Primary Examiner*—Ernest G. Therkorn
*Attorney, Agent, or Firm*—Vinson & Elkins

[57] ABSTRACT

An improved liquid filtering assembly used in applications such as filtering solvents for use in a liquid chromatography system. The filter assembly uses a filter cup having a large surface area which can be quickly removed and changed. The filter assembly also allows for the liquid to be drawn close to the bottom of the liquid reservoir. The filter assembly includes a coupling nut into which the tubing is secured on one side and an expansion member is secured on the other side. A seal ring is located around a portion of the expansion member. The expansion member urges the seal ring against the interior surface of the filter cup to secure the filter cup to the filter assembly. When the filter cup becomes clogged, the expansion member can be loosened to allow an operator to remove the clogged filter cup, replace it with a new filter cup, and then tighten the expansion member. Thus, the filter assembly can be reused simply by replacing the filter cup.

2 Claims, 3 Drawing Sheets

INLET FILTER AND METHOD OF USING SAME

This application is a division of application Ser. No. 08/041,481, filed Apr. 1, 1993, now U.S. Pat. No. 5,366,620.

FIELD OF THE INVENTION

This invention relates generally to an improved inlet filter and method for filtering liquids. More particularly, this invention relates to an inlet filter which is useful in liquid transfer applications, such as liquid chromatography.

BACKGROUND OF THE INVENTION

Liquid chromatography (LC) is a well known technique for separating the constituent elements in a given sample. In a conventional LC system, a liquid solvent (often called the "mobile phase") is introduced from a solvent reservoir and delivered via tubing to a pump. Many different types of conventional LC systems and components for LC systems are commercially available from a number of vendors. For example, Millipore Corporation of Milford, Mass., Beckman Instruments of Fullerton, Calif., and Hewlett-Packard Company of Palo Alto, Calif., all sell LC systems, including pumps, sample injection valves, columns, and detectors, among other things.

In opt:ration, a pump in the conventional LC system creates a vacuum which sucks the solvent through the tubing (suction tubing) and into the pump. An inlet solvent filter assembly is connected to the suction tubing leading from the solvent reservoir to the pump. This filter assembly is placed directly in the solvent reservoir. The purpose of the inlet filter is to remove any particles from the solvent and prevent the particles from reaching valves in the pump. A secondary function of the inlet filter is to act as a "sinker" to hold the suction tube inlet at the bottom of the solvent reservoir, thereby avoiding the introduction of air into the suction tube and/or the pump.

In a conventional LC system, the solvent exits the pump under a higher pressure and then passes to the sample injection valve. As the name suggests, the sample injection valve allows an operator to inject a sample into the LC system, where the sample will be carried along with the mobile phase. After the sample injection valve, most conventional LC systems include a column. A typical column usually consists of a piece of steel tubing which has been packed with a "packing" material. The "packing" consists of the particulate material inside the column. Conventional packing materials usually consist of silica- or polymer-based particles, which are often chemically bonded with a chemical function. When the sample is carried through the column (along with the mobile phase), the various components (solutes) in the sample migrate through the packing within the column at different rates (i.e., there is differential migration of the solutes). Because of the different rates of movement, the components gradually separate as they move through the column. A more detailed description of the separation process can be found, among other places, in Chapters 2 and 5 of *Introduction to Modem Liquid Chromatography* (2d ed. 1979) by L. R. Snyder and J. J. Kirkland, which chapters are incorporated by reference herein.

Once the sample (with its components now separated) leaves the column, it flows with the mobile phase past a detector. The detector detects the presence of specific molecules or compounds. As discussed in Chapter 4 of *Introduction to Modem Liquid Chromatogaphy*, which chapter is incorporated by reference herein, two general types of detectors are used in conventional LC applications. One type measures a change in some overall physical property of the mobile phase and the sample (such as their refractive index). The other type measures only some property of the sample (such as the absorption of ultraviolet radiation). In essence, a conventional detector in an LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a conventional LC system will often include filters, check vanes, and the like in order to prevent contamination of the sample or damage to the LC system. It will be understood to those skilled in the art that, as used herein, the term "LC system" is intended in its broad sense to include all apparatus used in connection with liquid chromatography, whether made of only a few simple components or made of numerous, sophisticated components which are computer controlled or the like.

In the past, filter assemblies often included filtering elements which required specially designed fittings for the suction tube connection. These prior art filters either had a stem for the tubing connection or a flangeless fitting which received a threaded flangeless nut on the end of the tube. Because inlet filters eventually become clogged with particle build up, they need to be changed from time to time. Hence, the special design of such prior art filters make them expensive to replace when they need changing. In addition, these prior art filters require a great deal of time to change since the suction tube must be disconnected from the filter cup assembly and then reconnected to a new filter cup. Such wasted time is often at a premium because of the expensive nature of many LC systems; changing such filters often renders the entire LC system inoperative until the change was completed.

Another problem with many conventional inlet filters is that they do not draw solvent from the bottom of the solvent reservoir. The use of such filters often results in the waste of expensive solvents. One conventional filter which is designed to draw from the bottom of the reservoir is shown in Bulletin #197 of Altech Associates, Inc., which is incorporated by reference herein. The suction tubing connected to this particular filter assembly draws fluid through a flat, disk shaped filter element (i.e., a "frit"). This flat filter element has a limited filter surface area, and therefore tends to clog relatively quickly. Moreover, the frit cannot be easily replaced when it becomes clogged. Hence, such conventional filters lead to shorter time periods between filter changes and require the replacement of the entire filter assembly. Also, such filters do not have any mechanism to allow an operator to quickly disconnect the filter assembly in order to change the filter element. Because the filtering elements themselves cannot be easily replaced by an operator, the entire filter assembly must be discarded. Hence, such filters clog relatively quickly and, when they do, they must be replaced by an entirely new filter assembly, a costly and inefficient approach to providing a solvent filter.

Accordingly, it is an object of the invention to provide an improved inlet filter which is more efficient and uses replaceable filtering elements.

Another object of the invention is to provide an improved inlet filter wherein the filtering element can be more easily replaced by an operator.

Another object of the invention is to provide an improved inlet filter which uses a replaceable filtering element.

Still another object of the present invention is to provide an improved inlet filter in which the filtering element can be replaced without disconnecting the rest of the filter assembly from the suction tube.

Still another object of the present invention is to provide a cheaper inlet filter in which the filtering element can be easily replaced without discarding the entire filter assembly.

A further object of the invention is to provide an improved inlet filter which positions the inlet of the tube through which the filtered liquid is drawn near the bottom of the liquid reservoir.

Still another object of the invention is to provide an improved inlet filter which will assist an operator in positioning the suction tube inlet at the bottom of a liquid reservoir.

SUMMARY OF THE INVENTION

The present invention provides an improved inlet filter for filtering a liquid being drawn from a liquid reservoir through a suction tube, particularly a liquid solvent used in liquid chromatography systems. The improved inlet filter assembly of the present invention includes a filter cup that has an open cup shape, to provide a relatively large filtering surface area. A tube is secured to one end of a coupling nut, with an expansion member removably connected to the other end of the coupling nut. The expansion member holds a portion of a seal ring against the filter cup to removably secure the filter cup to the rest of the filter assembly. A seal ring provides a seal between the filter cup and the expansion member, so that all liquid drawn through a channel through the length of the expansion member (and thus suction tube) must pass through the filter cup. The expansion member and seal ring exert enough force to hold the filter cup in place in a way that allows an operator to detach the filter cup from the filter assembly without detaching the filter assembly from the suction tube. This construction enables an operator to remove a filter cup by loosening the coupling nut from the expansion member, then pulling the filter cup off of the seal ring. The operator can then install a new filter cup by placing the new filter cup's open end around the bottom portion of the seal ring, then pushing the filter cup towards the rest of the filter assembly until the filter cup's lip abuts a shoulder on the seal ring. The coupling nut can then be retightened to secure the filter cup to the filter assembly. The invention thus allows an operator to replace a clogged filter cup with a new filter cup, all without detaching the filter assembly from the suction tube.

DESCRIPTION OF THE PREFERRED EMBODIMENT

Figure 1:
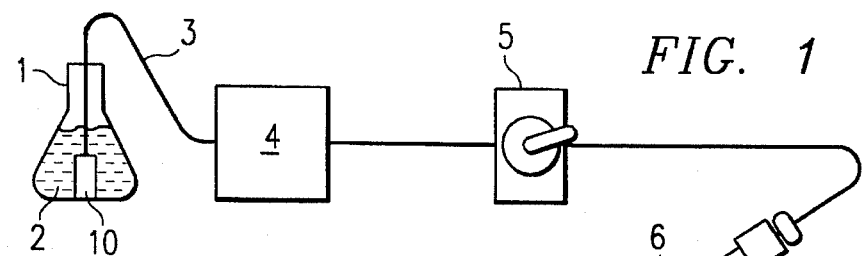
FIG. 1 is a schematic diagram of a typical application of the inlet filter of the present invention in a LC system.

FIG. 1 illustrates a basic LC system in which the present invention may be utilized. It will be understood, however, that the present invention may be used in a wide variety of applications, other than liquid chromatography, which involve liquid transfer. In FIG. 1, the filter assembly 10 is positioned in the liquid reservoir 1. Suction tubing 3 connects the filter assembly 10 and a pump 4. Pump 4 is of a type commonly known and used in LC systems. In operation, the pump 4 generates suction pressure through suction tubing 3 so that the liquid 2 (typically one of many types of solvents) in the reservoir 1 is drawn through the filter assembly 10, into suction tubing 3 and is delivered to the pump 4 and then throughout the remaining components of the LC system, such as through the sample injection valve 5, the column 6 and the detector 7. Still referring to FIG. 1, pump 4 is connected to a sample injection valve 5 which, in turn, is connected via tubing to a first end of a column 6. The second end of the column 6 is then connected via tubing to a detector 7. After passing through the detector 7, the mobile phase and the sample injected via injection valve 5 are deposited in a second liquid reservoir 8, which contains waste 9. Tubing is used to connect the various elements of the LC system together. As noted above, FIG. 1 merely illustrates a simplified LC system. It will be obvious that the inlet filter assembly 10 of the present invention will be useful in other applications.

Figure 2:
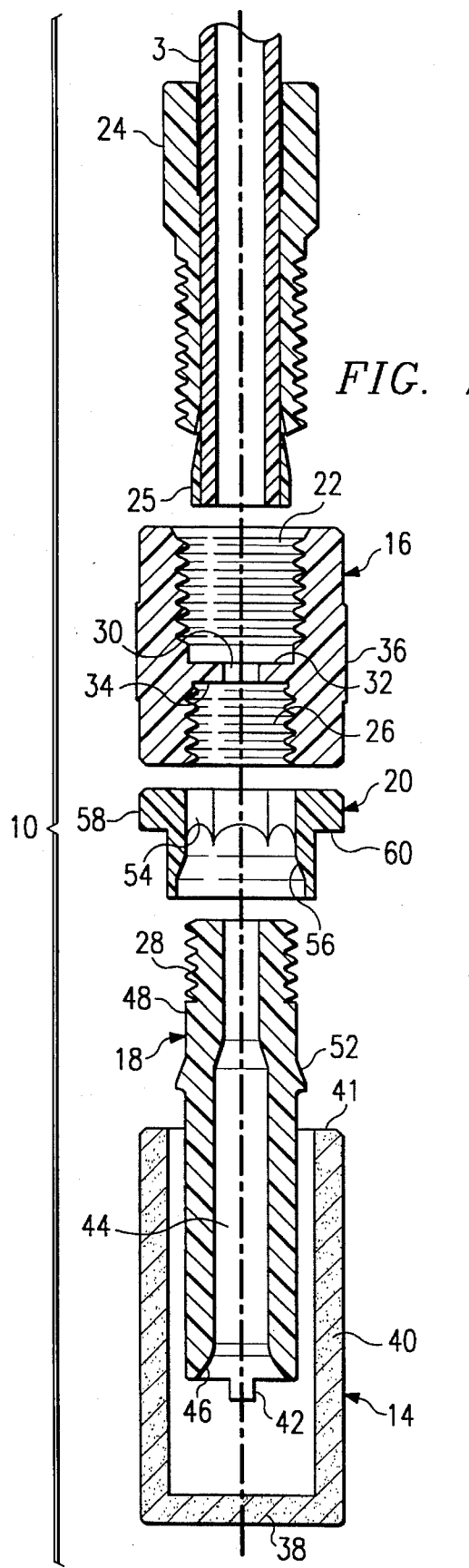
FIG. 2 is an exploded sectional view of the preferred embodiment of the inlet filter of the present invention.

An exploded view of the individual components of the preferred embodiment of the filter assembly 10 is shown in FIG. 2. Starting from the top of FIG. 2 and going down, FIG. 2 illustrates the following elements of the filter assembly 10. The suction tubing 3 is inserted through a fitting 24 and then through a ferrule or wedging ring 25. Next, the coupling nut 16 is shown; the coupling nut 16 includes both upper and lower threaded counterbores 22 and 26, respectively. A central bore 30 allows fluid communication between the threaded counterbores 22 and 26.

Figure 6:
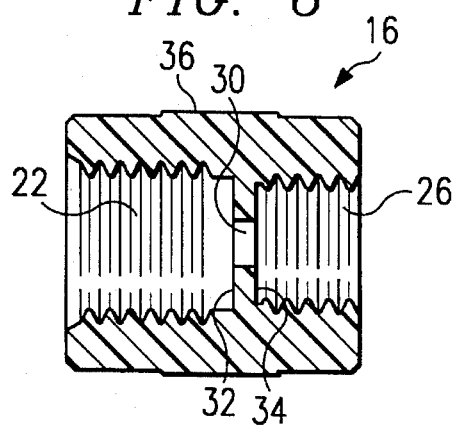
FIG. 6 is a sectional view of the coupling nut.
Figure 7:
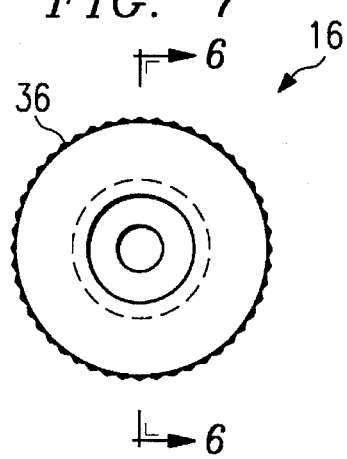
FIG. 7 is a top view of the coupling nut.

FIG. 6 shows coupling nut 16 in greater detail. Coupling nut 16 has a central bore 30 connecting the upper and lower threaded counterbores 22 and 26, respectively, which terminate in shoulders 32 and 34, respectively. Upper threaded counterbore 22 is designed to engage and mate with the threaded fitting 24 (as shown in FIG. 2). The lower threaded counterbore 26 is designed to engage and mate with threaded head 28 of the expansion member 18 (also shown in FIG. 2). As shown in FIG. 7, a portion of the outside surface 36 of coupling nut 16 has serrations 36. The serrations 36 are useful for gripping coupling nut 16 when an operator is loosening or tightening filter assembly 10. Coupling nut 16 is preferably made of a chemically inert plastic, such as the material polyetheretherketone, which is sold under the trademark "PEEK" and is commercially available from ICI Americas. As noted above with respect to the expansion member 18, however, many other suitable materials could be used for the coupling nut 16.

Figure 3:
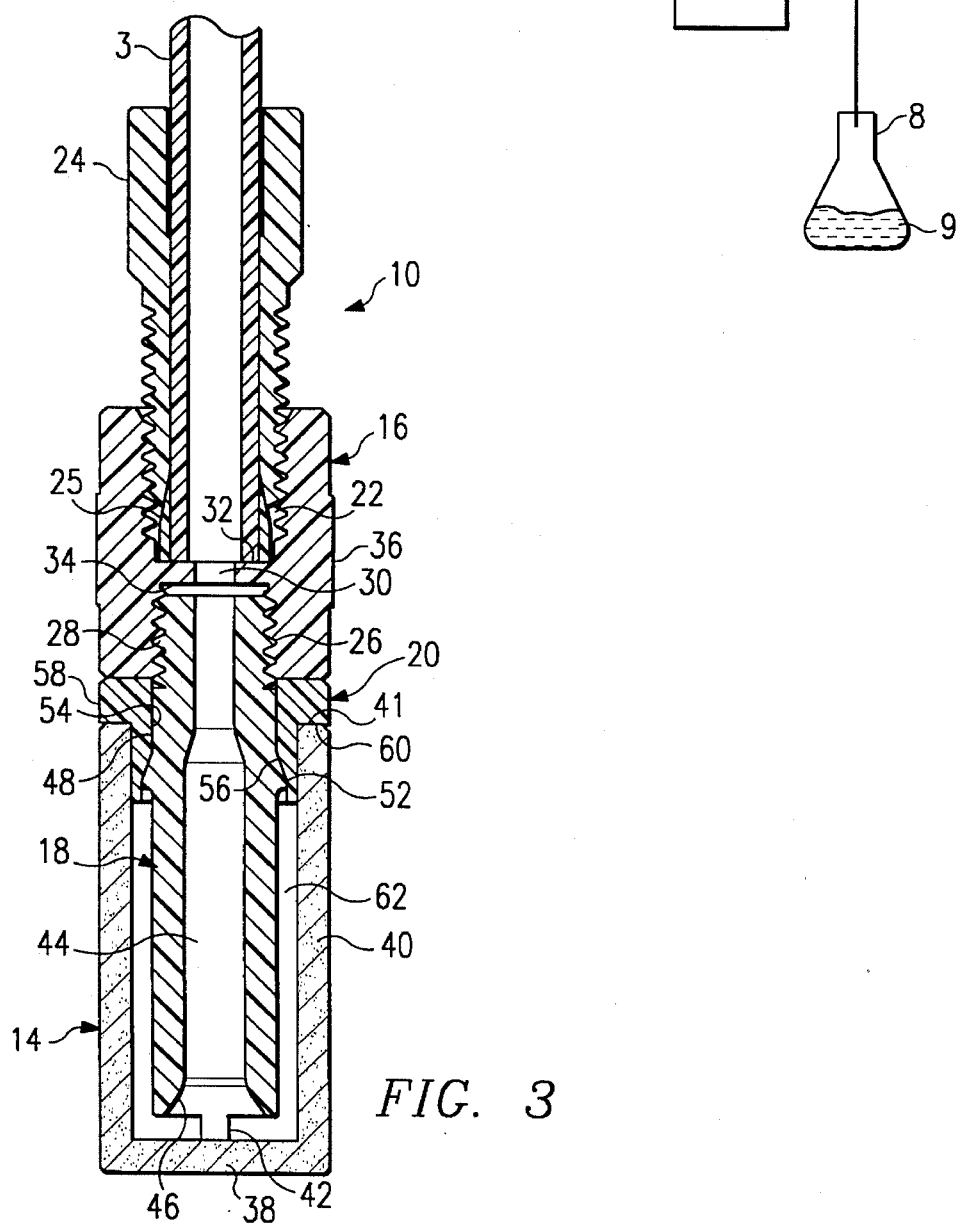
FIG. 3 is a sectional view of the preferred embodiment of the inlet filter of the present invention, which shows the inlet filter as assembled and connected to the suction tubing.
Figure 8:
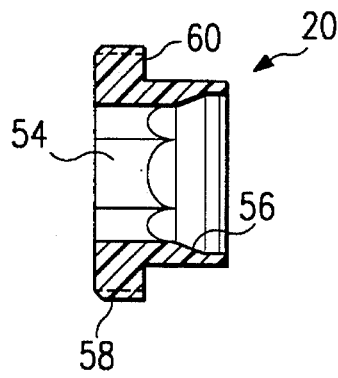
FIG. 8 is a sectional view of the seal ting.
Figure 9:
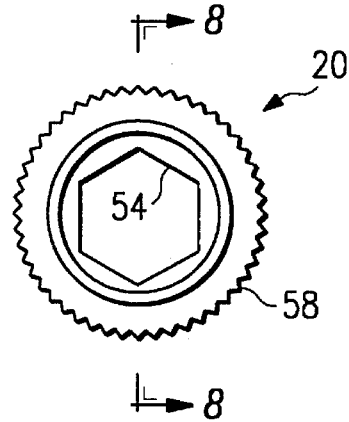
FIG. 9 is a bottom view of the seal ring.

In FIG. 2, a seal ring 20 is located below the coupling nut 16. As shown in FIG. 2, the seal ring 20 has a hollow interior which accepts and holds the neck 48 and the tapered shoulder 52 of the expansion member 18. Referring now to FIGS. 8 and 9, the seal ring 20 is shown in additional detail. The interior of the seal ring 20 has an upper portion 54 and a lower portion 56. Upper portion 54 is designed to engage and mate with the neck 48 of expansion member 18 (not shown in FIG. 8 or FIG. 9). Preferably, the upper portion 54 of the seal ring 20 (and also the neck 48 of expansion member 18) is hexagonal. Hence, when the threaded head 28 of the expansion member 18 is screwed into the lower counterbore 26 of the coupling nut 16 (as is shown in FIG. 3), the seal ring 20 and the expansion member 18 must rotate together. As shown in FIG. 8, the lower portion 56 of the seal ring 20 has a roughly conical shape and is designed to fit snugly around the tapered surface 52 of the expansion member 18 (not shown in FIG. 8). The outer surface of the seal ring 20 has serrations 58, which allow an operator to easily grip seal ring 20 when the operator is tightening or loosening the expansion member 18 from the coupling nut 16. Because the seal ring 20 and expansion member 18 are fixed with respect to each other, an operator can turn the seal ring 20 and thereby either tighten or loosen the threaded head 28 of the expansion member 18 when it is attached to the coupling nut 16. Seal ring 20 also has a shoulder 60 which, when the filter assembly 10 is fully assembled, abuts lip 41 of the filter cup 14 (as shown in FIG. 3). I prefer to use a seal ring 20 made of a resilient polymeric material, such as ethylene-tetrafluoroethylene, which is commercially available under the trademark "TEFZEL" from Du Pont. However, it is to be noted that other suitable materials could be used.

Figure 4:
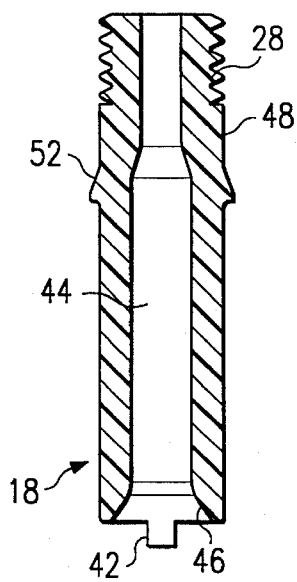
FIG. 4 is a sectional view of the expansion member.
Figure 5:
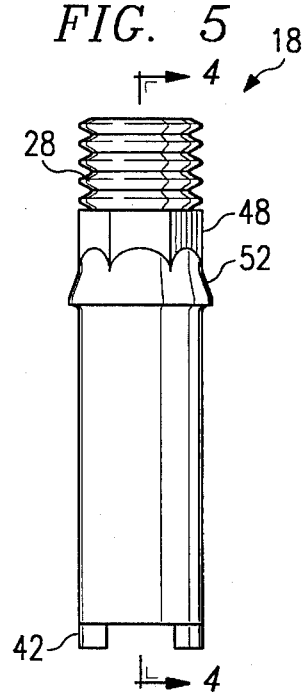
FIG. 5 is a side view of the expansion member.

In FIG. 2, the expansion member 18 is show beneath the seal ring 20. The expansion member 18 also has a threaded head 28 which can be screwed into the lower counterbore 26 of the coupling nut 16. Referring now to FIG. 4 and FIG. 5, the expansion member 18 is shown. The expansion member 18 has a generally tubular body with one end having a threaded head 28, a hexagonal neck 48, and a tapered surface 52. At its second end, the expansion member 18 has legs 42 and a flared inlet 46. As shown in FIG. 4, a tubular channel 44 runs from flared inlet 46 at the second end through the entire body of expansion member 18. As noted above, the threaded head 28 is designed to engage and mate with the lower threaded counterbore 26 of the coupling nut 16 (not shown in FIG. 4) in order to allow an operator to removably secure the expansion member 18 to the coupling nut 16 by screwing them together. As noted above, when the expansion member 18 has been screwed into the coupling nut (as shown in FIG. 3), the tapered surface 52 of the expansion member 18 engages lower portion 56 of seal ring 20 (as is shown in FIG. 3).

In the preferred embodiment, expansion member 18 is made of a rigid, chemically inert polymeric material, such as polyetheretherketone, which is commercially available under the trademark "PEEK" from ICI Americas. However, it is noted that other suitable materials could be used, such as metal or other plastics. Making expansion member 18 out of PEEK is advantageous because PEEK is chemically inert to most solvents used in liquid chromatography and is a "biocompatible" material; i.e., it will not distort the results of LC testing on biological samples. At the same time, however, PEEK is strong enough to withstand the relatively higher pressures which are often used in LC applications.

The filter assembly 10 includes at its lower end a generally cylindrical filter cup 14, which has an open end into which the lower portion of the seal ring 20 and the expansion member 18 are fitted (as detailed below). As shown in FIG. 2 and discussed in more detail below, filter cup 14 has a base 38, a cylindrical body 40, a lip 41 and an open top. Filter cup 14 preferably is a unitary component of porous filtering material. In the preferred embodiment, porous stainless steel is used, which is capable of screening particles larger than 10 microns. A porous stainless steel filter cup 14 which is capable of screening particles larger than 2 microns can also be used for many applications. Such porous stainless steel filter cups can be readily obtained from commercially available sources, such as Mott Metallurgical Corporation of Farmington, Conn. Alternatively, other suitable filter materials, such as porous titanium or polymeric materials such as polytetrafluoroethylene, which is commercially available under the trademark "TEFLON," or polyetheretherketone alloyed teflon, which is commercially available under the trademark "PAT," could be used. As another alternative, the filter cup 14 can be made of ultra-high molecular weight polyethylene "UHMWPE"), or of a ceramic material, such as alumina. Such materials are also commercially available from a variety of sources. Materials with pores of different sizes can be used for the filtering material. Although the filter cup 14 is shown in FIG. 2 as a unitary piece made of a single material, it is noted that filter cup 14 could be made of more than one material, or of more than one piece.

FIG. 3 now shows the elements of filter assembly 10 as assembled together. A discussion of the assembly of the filter assembly 10 according to the preferred embodiment of the invention follows. The tubing 3 is connected to the filter assembly 10 in the following manner. The fitting 24 is placed over the end of the tubing 3, and then the wedging ting 25 follows the fitting 24 onto the end of the tubing 3. The combination of the end of the tubing 3, the wedging ring 25, and the fitting 24 are then inserted into the upper counterbore 22 of the coupling nut 16. The threaded exterior of the fitting 24 is then screwed into the upper threaded counterbore 22 of the coupling nut 16 until wedging ring 25 pinches against the tubing 3 and the fitting 24 is firmly and securely attached to the coupling nut 16. By tightening the fitting 24 into the upper threaded counterbore 22, the fitting 24 also secures one end of the tubing 3 and the wedging ring 25 firmly against the bottom 32 of the upper counterbore 22 of the coupling nut 16. The wedging ring 25 provides a seal between the interior of the tubing 3 and the upper threaded counterbore 22. It is to be noted that other fittings and connecting means could alternatively be used to connect the suction tubing 3 to the coupling nut 16. The fitting 24, according to this embodiment of the invention, however, provides the advantage of allowing the operator to loosen the connection and detach the tubing 3 if the operator chooses to do so (such as would be the case if the operator decided to switch a piece of plastic tubing for metal tubings or vice versa).

Continuing to refer to FIG. 3, the remainder of the filter assembly 10 is assembled in the following manner. The seal ring 20 is placed over the threaded head 28 of the expansion member 18, so that the threaded head 28 extends through the top, open end of the seal ring 20. The seal ring 20 is designed so that it engages the neck 48 of expansion member 18 such that the inner surface of upper portion 54 of the seal ring 20 snugly fits around the neck 48 of the expansion member 18. Similarly, the inner surface of the lower portion 56 of the seal ring 20 fits snugly around tapered surface 52 of the expansion member 18. Next, the threaded head 28 of the expansion member 18 is inserted and threaded into the lower threaded counterbore 26 of the coupling nut 16 until the expansion member 18 is securely fastened to the coupling nut 16. At this point, the top end of the seal ring 20 is held firmly against the bottom of the coupling nut 16.

As shown in FIG. 3, the tapered surface 52 of the expansion member 18 is designed to that the tapered surface 52 is extended further and further into the lower portion 56 of the seal ting 20 as the threaded head 28 is screwed into the lower counterbore 26. Accordingly, the tapered surface 52 pushes harder and harder against the inner surface of the lower portion 56 as the threaded head 28 is screwed further into the lower counterbore 26. Conversely, when the expansion member 18 is unscrewed from the lower counterbore 26, the lower portion 56 of the seal ring 20 has the ability to separate more and more from the tapered surface 52 of the expansion member 18, thus decreasing the force of the expansion member 18 against the inner surface of the lower portion 56 of the seal ring 20. Consequently, it will be understood that the filter cup 14 is more securely held by the seal ting 20 when the threaded head 28 of the expansion member 18 is firmly screwed into the lower counterbore 26, whereas the filter cup 14 is held more loosely by (and therefore more easily removed from) the seal ring 20 when the threaded bore 28 is partially or completely unscrewed from the lower counterbore 26.

The last step in assembling the filter assembly 10 is placing the filter cup 14 on the bottom of the filter assembly 10. For the reasons noted above, it is easier to assemble the filter assembly 10 if the threaded head 28 is first slightly unscrewed (by ¼ to ½ of a turn) from the lower counterbore 26. At this point, the open end of the filter cup 14 is placed around the bottom edge of the seal ring 20. The filter cup 14 can then be pushed manually onto the filter assembly 10 until the lip 41 of the filter cup 14 abuts the shoulder 60 of the seal ring 20. At this point, the tapered surface 52 of expansion member 18 pushes outwardly against lower portion 56 of seal ring 20, as is shown in FIG. 3. The lower portion 56 of the seal ring, in turn, is compressed and pushes outwardly against the inner surface 40 of the filter cup 14. As detailed above, an operator can then screw the threaded head 28 firmly into the lower counterbore 26, thus increasing the outward pressure exerted by the seal ring 20 on the filter cup 14. This pressure securely holds the filter cup 14 in place as a pan of the filter assembly 10.

Once the filter assembly 10 has been assemble& it can be used to filter a liquid in the following manner. Although the following discussion addresses the use of the filter assembly 10 in a liquid chromatography system, it will be understood that the filter assembly 10 can be used in other fluid transfer applications. Referring back to FIG. 1, the pump 4 creates a suction pressure in tubing 3, which draws the liquid through the filter assembly 10 and to the pump 4 through the tubing 3. Referring to FIG. 3, the suction pressure is transferred via tubing 3 through the chamber 30 of the coupling nut 16, and then through the tubular channel 44 in the expansion member 18 to flared inlet 46. The legs 42 of the expansion member 18 (shown in FIG. 3) help prevent the flared inlet 46 from resting directly on the inside surface of the base 38 of filter cup 14. This allows the free flow of liquid into flared inlet 46 through a greater amount of surface area of the filter cup 14. This approach decreases the possibility that a relatively small surface area of the filtering element will become plugged and thus render the entire filter cup 14 unusable. This increases the amount of time a given filter cup 14 can be used before it needs to be replaced. Of course, a filter cup 14 in which only certain areas or portions are porous (and thus filter the liquid) could be used.

As shown in FIG. 3, a cavity 62 is formed between the inner surface of the cylindrical body 40 of the filter cup 14 and the outer surface of expansion member 18. During the operation of the filter assembly 10, the suction pressure draws the liquid through the porous material of filter cup 14, thereby screening any particles larger than the pores. The filtered liquid then enters cavity 62. The suction pressure at flared inlet 46 draws the filtered liquid in from cavity 62 and up through expansion member 18, through coupling nut 16 and into the tubing 3, through which the liquid is carried to the pump 4 (as show in FIG. 1).

The outward pressure of the seal ring 20 against the inner surface of the body 40 of the filter cup 14 creates a seal which prevents unfiltered liquid from entering the cavity 62. This sealing action keeps filter assembly 10 air tight, thereby allowing the filtered liquid to be drawn into flared inlet 46.

Referring still to FIG. 3, filter assembly 10 allows liquid to be drawn from a point close to the bottom of the liquid reservoir 1 (which is shown in FIG. 1). As discussed earlier, since the suction pressure in tubing 3 is transferred to flared inlet 46 and since the legs 42 of the expansion member 18 keep the flared inlet 46 raised slightly away from the inside surface of the base 38 of the filter cup 14, the suction pressure for drawing in the liquid is located at a point just above base 38. If the filter assembly 10 is placed with a liquid reservoir 1 so that the bottom of the filter cup 14 rests on the bottom of liquid reservoir 1, liquid can be drawn through the flared inlet 46 until the fluid level outside filter cup 14 reaches a depth approximately equal to the distance that the flared inlet 46 is above the bottom of liquid reservoir 1. This allows the operator to use as much of the solvent 2 as possible, thereby minimizing the waste of expensive solvents.

Another advantage of the improved filter assembly 10 is the speed and ease with which filter cup 14 can be changed, as well as the fact that the filter assembly 10 can be reused by simply replacing the filter cup 14. When the filter assembly 10 is used, it will tend to become clogged as particles become trapped in filter cup 14. Over time, more and more particles will be trapped. Eventually, the filter cup 14 will need to be replaced when it becomes sufficiently plugged with particles screened from the liquid passing through filter cup 14 so that the liquid flow through filter 14 becomes impaired.

The following is a discussion of the replacement of a clogged filter cup 14 with a new filter cup 14. Referring now to FIG. 3, the following is a discussion of how to first remove the used filter cup 14. First an operator loosens the coupling nut 16 by unscrewing it a quarter to a half turn from the threaded head 28 of expansion member 18. The operator can do this by unscrewing the coupling nut 16 while holding the seal ring 20 or vice versa. While unscrewing coupling nut 16, the serrations 36 on the coupling nut 16 and the serrations 58 on the seal ting 20 can be gripped. As noted above, the seal ring 20 and expansion member 18 are held stationary with respect to one another because of the mating of the hexagonal surfaces of the upper portion 54 and the neck 48. Once the coupling nut 16 has been so loosened from the expansion member 18, the expanded lower portion 56 of seal ring 20 can move away from the tapered surface 52 of the expansion member 18 to thereby relieve the outward pressure against the inside of body 40 of the filter cup 14. The used filter cup 14 can now be easily removed manually by pulling the filter cup 14 in the direction away from the rest of the filter assembly 10.

To replace the filter cup 14, the following steps can be used. A new filter cup 14 can be placed over the expansion member 18 until the new filter cup 14 abuts shoulder 60 of seal ring 20. By screwing the coupling nut 16 a quarter turn to a half turn back onto the threaded head 28, the new filter cup 14 can be locked into place. As before, the outward pressure now exerted by the outside of the lower portion 56 of the seal ring 20 (which is due to the outward pressure exerted by the tapered expansion surface 52 of the expansion member 18) against the interior surface of the filter cup 14 keeps the filter cup 14 firmly attached to the rest of the filter assembly 10. One extremely convenient feature of the present invention is that, during the entire removal and replacement of the filter cup 14, the tubing 3 can remain connected to the rest of the filter assembly 10 (via upper threaded counterbore 22). Moreover, the removal and replacement of a filter cup 14 can be performed manually, thereby saving on costly downtime of the LC system and avoiding the need for any expensive tools. Hence, the present invention provides a more efficient filter assembly 10 which is also cheaper because it can be easily reused by replacing only the filter cup 14 when it becomes clogged.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiment and specific shapes, materials, and the like are merely illustrative and do not limit the scope of the invention or the claims herein.

What is claimed is:

1. A method of replacing a filtering element comprising the steps of:

loosening a coupling nut to which an expansion member which is removably attached to a filtering element has been removably attached;

removing the filtering element from a seal ring attached to the expansion member;

replacing the filtering element with a different filtering element; and tightening the coupling nut to secure the coupling nut to the expansion member and secure the seal ring to the filtering element.

2. The method according to claim 1 wherein the step of replacing the filtering element comprises the steps of:

positioning a different filtering element around at least a portion of the seal ring; and pressing the filtering element over the seal ring.

\* \* \* \* \*